United States Patent [19]

Narayanan

[11] Patent Number: 5,766,615

[45] Date of Patent: Jun. 16, 1998

[54] COMPOSITIONS OF INSOLUBLE FILM-FORMING POLYMERS AND USES THEREFOR

[75] Inventor: Kolazi S. Narayanan, Palisades Park, N.J.

[73] Assignee: ISP Investments Inc., Wilmington, Del.

[21] Appl. No.: 975,811

[22] Filed: Nov. 13, 1992

[51] Int. Cl.$^6$ ............... A01N 25/04; A01N 25/14; A01N 25/30; A01N 25/24

[52] U.S. Cl. ............... 424/405; 424/407; 424/409; 71/64.02; 71/64.07; 71/64.1; 71/DIG. 1; 523/122; 514/937; 514/938; 504/113

[58] Field of Search ............... 514/772.5; 424/405, 424/407, 409, 717, 78.18, 78.22; 252/357; 71/64.02, 64.04, 64.1, DIG. 1; 525/66, 69; 526/264; 523/122; 428/402

[56] References Cited

U.S. PATENT DOCUMENTS

| | | | |
|---|---|---|---|
| 4,482,534 | 11/1984 | Blank | 424/449 |
| 5,061,751 | 10/1991 | Patton | 524/33 |
| 5,071,463 | 12/1991 | Narayanan et al. | 514/788 |
| 5,093,031 | 3/1992 | Login et al. | 548/529 |

*Primary Examiner*—Edward J. Webman
*Attorney, Agent, or Firm*—William J. Davis; Jules E. Goldberg; Marilyn J. Maue

[57] ABSTRACT

A composition comprising a long-chain alkylpyrrolidone, a surfactant, and film-forming water-soluble polymer wherein the amounts of the components are such that on dilution with water, a clear liquid is formed. The composition may be used as a medium for agriculturally active ingredients as well as other active ingredients which are suitable for film formation, e.g., wood protectants, and the like.

31 Claims, No Drawings

COMPOSITIONS OF INSOLUBLE FILM-FORMING POLYMERS AND USES THEREFOR

BACKGROUND OF THE INVENTION

Certain types of polymers exhibit film-forming properties and when dissolved in a solvent, can be applied for the purpose of providing a coating on a substrate. Usually, the film-forming polymer in the solvent is applied to the particular substrate to be coated, and the solvent is allowed to evaporate or removed leaving a film of the polymer. Generally, however, such film-forming polymers are soluble only in organic solvents. The use of such organic solvents generally is undesirable since they exhibit environmentally adverse properties, are often hazardous or flammable, and are generally expensive. In order to avoid the environmentally adverse effects of such organic solvents as well as to reduce the cost involved with using such solvents, rather complicated solvent recovery procedures must be used.

Typical of such polymers are copolymers of N-vinylpyrrolidone with α-olefins, vinyl acetate, styrene, acrylates, acrylic acids, amides, maleic acid, mono and diesters of maleic acids, and the like.

SUMMARY OF THE INVENTION

I have discovered a method for providing a stable microemulsion of a particular class of water-insoluble film-forming polymers in water. The microemulsions thus formed, can be utilized to produce films of the particular film-forming polymer on a given substrate. For example, the microemulsion can be used as a coating for substrates, such as, wood, metal, glass, and the like. In addition, various active ingredient, e.g., fungicides, preservatives, insecticides, insect repellents, pheromones, radiation absorbents, dyes, and the like, can be included in the composition.

The inventive compositions are composed of the water-insoluble polymer, a surfactant, and a long-chain alkylpyrrolidone. The amounts of the polymer surfactant and long-chain alkylpyrrolidone can vary within a broad range. However, the relative compositional ranges of each must be such that a clear, stable microemulsion or solution of the insoluble polymer is obtained on the addition of water.

The water-insoluble polymer used in the present invention are graft polymer vinylpyrrolidone and α-olefin wherein the N-vinylpyrrolidone is present in more than 20 percent on a weight basis. Preferably, the weight percent of N-vinyl pyrrolidone is at least 50 percent. The α-olefin should contain up to 20 carbon atoms.

I have further discovered that the aqueous microemulsion compositions of the invention are particularly suitable for use with an agriculturally active chemical or ingredient (hereinafter, sometimes referred to as a.i.). Thus, the inventive composition of the film-forming polymer may also include an agriculturally active chemical or ingredient, such as, pesticides, herbicides, and the like. This composition may then be applied to plants, or soil, in the usual manner. I have found that the inventive composition, thus used, forms a film incorporating the a.i. on the leaf, soil or seeds and can prevent wash-out of the agriculturally active ingredient due to rain. Thus, for example, the composition with an agriculturally active ingredient forms a film on the particular substrate, e.g., the plant or soil, which results in improved retention and enhanced bioactivity of the agriculturally active ingredient and also provides superior rainfastness for such ingredients on leaf and substrate surfaces.

DETAILED DESCRIPTION OF THE INVENTION

As used herein, the following terms have the meaning indicated:

"macroemulsion" means an emulsion of water-in-oil or oil-in-water wherein the interior phase is in the form of visually discernable droplets and the overall emulsion is cloudy, and wherein the droplet diameter is greater than about 10 millimicrons, and usually greater than 1000 millimicrons.

"microemulsion" means an oil-in-water or water-in-oil, transparent thermodynamically stable dispersion of two or more immiscible liquids or a solid in a liquid wherein the dispersed phase consists of small droplets with diameters in the range of about 10 to 100 millimicrons. Such microemulsions are clear and appear as a single phase to the naked eye.

"single phase" as applied to a liquid means that to the naked eye, the liquid is homogeneous and does not appear to contain any other separatable liquid phase.

"clear" or "transparent" as applied to a liquid means that the liquid appears as a single phase without any particulate or colloidal material or a second phase being present when viewed by the naked eye.

"substantially insoluble" or "insoluble" means that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

"High degree of loading in the concentrate" means an agriculturally active ingredient content of at least about 5 percent by weight.

"agriculturally active chemical or ingredient" (AAC or a.i.) means compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests.

Long-chain N-alkylpyrrolidones suitable for use in the present invention have the formula

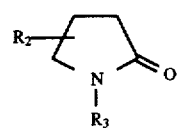

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14. Preferably, $R_2$ is hydrogen and $R_3$ is $C_8$ or C12. Mixtures of two long-chain alkylpyrrolidones may also be used. N-methyl pyrrolidone may also be included along with long chain N-alkylpyrrolidones in an amount effective to help maintain the solubility of the long chain alkylpyrrolidones.

Surfactants suitable for use in the inventive composition include ethoxylated alkyl phenols, linear aliphatic polyesters, linear aromatic polyesters, polyalkenyloxyalcohol, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfates, sulfonates, and their salts, salts of sulfate nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergents* (1989), published by McCutcheon's Division of M.C. Publishing Co., Glen Rock, N.J.)

Polymers particularly suitable for use in the present invention include polymers, such as, Ganex 516, which is copolymer of an α-olefin and N-vinylpyrrolidone (50/50 percent mixture). Typically, such α-olefins contain up to 20 carbon atoms and preferably, contain 16. The weight average molecular weight of such polymers is generally greater than about 20,000. Particularly suitable are water-insoluble polymers, such as, Agrimer AL25 (International Specialty Products (ISP) Corporation), which is a copolymer of an α-olefin having the formula $C_{14}H_{29}CH=CH_2$ (50%) and N-vinylpyrrolidone (50%), and Agrimer AL30 (ISP Corporation), which is a copolymer of an α-olefin having 20 carbon atoms (80%), and N-vinylpyrrolidone (20%). All percents herein are percent by weight based on the total weight of the composition.

Typically, the composition of the invention comprises from about 2 to 90 percent, and preferably, from about 30 to 60 percent by weight N-alkyl pyrrolidone; from about 2 to 30 and preferably, from about 8 to 15 percent by weight surfactant and from about 1 to 60, and preferably from about 5 to 30 percent, and most preferably, 10 to 20 weight percent of the water insoluble polymer, and from about 0 to 50 percent, and preferably, about 20 to 30 percent by weight water.

The inventive compositions are particularly suitable for end use applications wherein films of water-insoluble polymers are formed on substrates. The films may be formed for adhesive, protective, decorative, lubricating, to impart hydrophobicity or hydrophilicity, and the like, purposes. Since it is desirable to avoid organic solvents due to their cost and adverse toxicological and environmental properties, the use of water as a solvent for the film-making procedure is preferred. With the inventive composition, it becomes possible to place such ordinarily water-insoluble film-forming polymers in an aqueous based vehicle which can be handled and utilized in the same manner as a true solution of the polymer to form a film therewith. Thus, the inventive composition in microemulsion form may be coated as is, or after further dilution with water, if desired, onto a substrate. The water is then removed as by evaporation to leave the polymer film remaining.

I have further discovered that the rainfastness of agriculturally active ingredients, and in particular, pesticides, can be substantially improved by formulating the pesticides in the inventive composition including the water insoluble film-forming polymer. Thus, many pesticides, and particularly water soluble agriculturally active chemicals, are washed off by rain after they have been applied to the plants or soil. For effective pest and weed control, it takes from a few hours to three weeks for the pesticide to penetrate into the biological system. The present invention assures that the agriculturally active ingredient will be retained for a sufficiently long time to allow it to be effective and avoid or reduce rain wash-off.

In use, the inventive composition is diluted with water and applied to the crop, plants, or soil. Normally, this dilution is carried out at the field site. As used herein, rainfast resistant, rainfast or rainfastness in connection with the inventive compositions means that a film formed from the composition exhibits increased resistance to removal by water washing as compared to the same composition which does not contain the film-forming polymer under the test procedures as described hereinafter.

Pesticides which can be used with the present invention, may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into three groups:

The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenoxy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfonamide (BETASAN®),
Isobornyl Thiocyanoacetate (Thanite™),
Ioxynil ester of octanoic acid,
Molinate S-ethyl hexahydro-1 H - azepine-1-carbothioate,
PP 511 0,0-dimethyl-(2-diethylamine 4-methyl-6-pyrimidinyl) carbamate,
PP 211 0,0-diethyl o-(2-diethylamine-4-methyl-6-pyrimidinyl) phosphorocarbamate,
5-Ethoxy-3-(trichloromethyl)-1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamatae (TILLAM®),
S-ethyl ethylcyclohexylthiocarbamate (RO-NEET®),
Malathion (S-(1,2-dicarboxyethyl)-0,0-dimethyl phosphorodithioate),
Diazinon (0,0-diethyl,0-(2-isopropyl-4-methyl-6-pyrimidinyl) phosphorothioate,
O-Ethyl-S-phenyl-ethylphosphonodithioate (DYFONATE®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,3,3-trichloroallyl N,N-diisopropylthiol- carbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-triazine)
Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s-(o,o-dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl) dimethyl phosphorothiolthionate)
Barban (4-chloro-2 butynyl m-chlorocarbanilate)
Tricamba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methylpyrimidine*

* Manufactured by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclopentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy) phenyl] urea
Mecoprop 2-(4-chloro-2 methylphenoxy)propionic acid
Monolinuron N'-(4-chlorophenyl)-N-methoxy-N-methylurea
Nitrofen 2,4-dichlorophenyl 4-nitrophenylether
Propanil N-(3,4-dichlorophenyl)propionamide
Pyriclor 2,3,5-trichloro-4-pyridinol
Solan 3,-chloro-2--methyl-p-valerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide
Cypromid 3',4'-dichlorocyclopropane carboxanilide
Fenuron NN-dimethyl-N-phenylurea
Chlorbromuron N'-(4-bromo-3-chlorophenyl)-N-methoxy-N- methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzene
1-(butyl carbamoyl)-2-benzimidazole carbamic acid, methyl ester (BENLATE®).

The third group constitutes those compounds which are water-soluble, such as, salts, e.g., the isopropylamine salt of phosphonomethyl glycine, the sodium salt of 2,4-dichlorophenoxy acetic acid, the sodium salt of methoxy dichloro benzoic acid (dichloro anisic acid), and dicamba (dimethylamine salt of methoxy dichlorobenzoic acid). Assert bisulfate (American Cyanamid), the ammonium salt of imazaquin (American Cyanamid), and the like.

The following Examples illustrate the invention:

The materials used in the Examples and designated by trademark or tradename are as follows:

Agrimer AL25 copolymer of vinyl pyrrolidone and $C_{16}$ α-olefin in 50:50 weight ratio with a number average molecular weight of about 9500;

Agrimer AL30 graft copolymer containing 80% by weight of $C_{20}$ α-olefin and 20% by weight of polymerized vinylpyrrolidone with a number average molecular weight of about 8600 available as a solid;

Agrimer AL22 graft copolymer containing 80% by weight of $C_{16}$ α-olefin and 20% by weight of polymerized vinylpyrrolidone with a number average molecular weight of about 7300 available as a liquid;

Agrimer VA3 copolymer containing 30 mole % vinylpyrrolidone units and 70 mole % vinylacetate unit with a number average molecular weight of 5700 and weight average molecular weight of 28,800 determined by the GPC method;

Acrylidone

ACP-1004 copolymer containing 50:50 weight ratio of the monomer with number average molecular weight =30, 000–60,000, 100,000–300,000.

Rodeo a commercially available pesticide of an aqueous solution containing 53.8% of the isopropylamine salt of phosphonomethylglycine (a.i.–1) (Monsanto).

Latron B1956 77% modified phthalic glycol alkyl resin, and 23% inert ingredients including organic solvent (Rohm & Haas);

Prowl an emulsion concentrate containing 42.0% by wt. pendimethalin (a.i.–2). The balance constitutes surfactants and solvents.

Roundup a commercially available concentrate of glyphosate with suitable wetting agents. Glyphosate is the isopropylamine salt of phosphonomethylglycine.

Gramoxone a commercially available concentrate of Paraquat in suitable wetting agents.

Paraquat is 1,1-dimethyl-4,4'-bipyridinium dichloride (American Cyanamid).

EXAMPLE 1

Compositions containing water insoluble polymers in a water-based medium were prepared as follows:

Preparation of Matrix

In a 4 oz. stoppered glass bottle, 48.33 g of N-octylpyrrolidone, and 41.67 g of a 29% by weight aqueous solution of sodium dodecyl sulfate (commercially available) were added and stirred to form a homogeneous solution containing 48.33 g of N-octylpyrrolidone, 12.06 g of sodium dodecyl sulfate and 29.61 g water. This solution is referred to herein as the stock matrix solution. To 90 g of the stock matrix solution were added 10 g of the dry water-insoluble Agrimer AL25. The solution was stirred in an automatic orbital shaker at 400 RPM for a period of 3 hours, which produced a homogeneous single phase system. On 10×, 500× and 1000×dilution with deionized water, the diluted composition remained homogeneous for more than 72 hours. The dry Agrimer AL25 was prepared by evaporation of the commercially available 50 percent solution of AL25 in isopropyl alcohol under reduced pressure, drying the residue in vacuum oven at about 60–70° C. at 1 mm Hg., and then grinding under a blanket of liquid nitrogen to produce a particulate solid.

EXAMPLE 2

Example 1 was repeated using 85 parts of stock matrix solution and 15 parts of the polymer. The resulting composition is shown in Table 1 and is referred to herein as Composition I. This composition was also in a homogeneous single phase system. On 10×, 500×, and 1,000×dilution with deionized water, the diluted composition remained homogeneous for more than 72 hours.

EXAMPLE 3

Example 1 was repeated using 80 parts of stock matrix solution and 20 parts of the polymer. The resulting composition is shown in Table 1. At 10× and 500×dilution with deionized water, the compositions produced exhibited no separation for more than 72 hours. When 1 part of the composition was diluted to 1000 parts with deionized water, a single minute crystal was observed.

TABLE 1

Compositions of a Single Phase System
Containing Agrimer AL25 in an Aqueous Medium

| Composition, Ingredients | Weight % | | |
|---|---|---|---|
| | Example 1 | Example 2 | Example 3 |
| N-octylpyrrolidone (LP-100) | 48.33 | 45.65 | 42.96 |
| Sodium dodecylsulfate (SDS) | 12.06 | 11.39 | 10.72 |
| Agrimer AL25 | 10.00 | 15.00 | 20.00 |
| Water | 29.61 | 27.96 | 26.32 |
| TOTAL | 100.00 | 100.00 | 100.00 |
| Physical State | single phase | single phase | single phase |
| Dilution with deionized | | | |

TABLE 1-continued

Compositions of a Single Phase System
Containing Agrimer AL25 in an Aqueous Medium

| Composition, Ingredients | Weight % | | |
|---|---|---|---|
| | Example 1 | Example 2 | Example 3 |
| water | | | |
| 1/10 | | single phase | |
| 1/500 | single phase | single phase | single phase |
| 1/1000 | single phase | single phase | single phase* |

*single phase with minute crystal separations

EXAMPLE 4

This example illustrates the inability of an isopropyl alcohol (IPA) solution of Agrimer AL25 to remain homogeneous in the absence of the inventive stock matrix. A composition was prepared by mixing 40 g of a 50% solution of Agrimer AL25 in IPA, 35.72 g of a 29% aqueous SDS solution and 24.20 g of deionized water. The resulting composition contained by weight: 25% Agrimer AL25, 20% IPA, 10.36% SDS, and 49.64% water. The resulting product was a milky, cloudy emulsion. Microscopic observation at 250×showed particles/oil droplets of about 5–10 µ in size.

Examples 5 through 9 illustrate the importance of the presence of more than 20% on a weight basis of vinyl pyrrolidone in the copolymer.

EXAMPLE 5

90 parts stock matrix solution, and 10 parts of Agrimer AL30 were mixed in an automatic orbital shaker for 4 hours. No dissolution occurred.

EXAMPLE 6

Example 5 was repeated replacing Agrimer AL30 with 10 g of Agrimer AL22. After stirring for 4 hours in an automatic orbital shaker, oil separation was observed.

EXAMPLE 7

Example 4 was repeated using 98 parts of stock matrix solution and 2 parts of Agrimer VA3. The composition did not produce a single phase system on stirring in an automatic orbital shaker for 4 hours.

EXAMPLE 8

Example 4 was repeated with 95 parts of stock matrix solution and 5 parts of Acrylidone ACP-1004. A homogeneous phase was not obtained after 4 hours of stirring.

EXAMPLE 9

Example 4 was repeated using 95 parts of stock matrix solution and 5 parts of cross-linked polyvinylpyrrolidone with a molecular weight of about 1 MM. A single phase system was not obtained. However, the polymer was wetted by the matrix.

Part A

A series of polymer films formed from the inventive composition were evaluated for rain-fastness. The formulations were prepared as follows:

1. A commercial formulation of a given agriculturally active ingredient was admixed with the inventive composition.
2. The liquid mixture was then diluted to end use concentrations.
3. An appropriate dose (0.1 g to 0.5 g) was applied to a 6"×6" glass plate uniformly as a 1–3" square patch. The patch was dried in a hood under ambient conditions for 48–72 hours.
4. After a dry film was formed, a fine spray of water was applied to simulate 0.5–2 inches of rain wash-off. The washings were collected in a waste jar.
5. The remaining washed patch was extracted with a solvent (ethanol is preferred) quantitatively into a 100 ml volumetric flask. If desired, appropriate dilutions of the ethanol extract were made.
6. The ethanol extract was subjected to ultraviolet spectra examination and the absorbance at a λ max. was determined (value $X_1$).
7. Blank samples of diluted formulations were prepared and measured using UV absorption. These values were utilized to prepare a calibration chart. This value is $X_2$.
8. The percent retained was then determined by dividing $X_1$ by $X_2$ and multiplying by 100.
9. Blanks were run without polymer using the commercial formulations under identical conditions. The percent retained is identified as $R_b$.
10. For samples wherein the pesticide used is Pendimethalin, λ max. is 239 nm. 0.3 g of diluted samples were used for patches (1–2 square inches). The amount of wash-off water used was 1.5 to 2.5 g.

Using this technique, a series of compositions were formulated and tested for retention of the active ingredient.

Part B
Rainfast evaluations

The following solutions were prepared:

Solution 9A 4.0036 g of Rodeo was diluted to 100 g with deionized water. This solution contained 2.15% a.i.–1. on a weight basis.

Solution 9B 4.0101 g Rodeo was mixed with 0.13 g of Composition I and diluted to 100 g with deionized water producing a clear solution.

Solution 9C 4.0033 g Rodeo was mixed with 0.34 g of Composition I and diluted to 100 g with deionized water producing a clear solution.

Solution 9C 4.0095 g Rodeo was mixed with 0.66 g of Composition I and diluted to 100 g with deionized water producing a clear solution.

Samples of solutions 9A, 9B, 9C, and 9D were analyzed for the a.i.–1. content via potentiometric titration using standard NaOH (0.0217N). The NaOH was standardized using a standard solution of sodium hydrogen phthalate. For 0.6911 g of 9A, 0.7044 g of 9B, and 0.7189 g of 9D, 3.00 ml of NaOH was required. For 0.7045 g of 9C, 2.95 ml of the NaOH solution was required for neutralization. The % a.i.–1. for the samples 9A, 9B, 9C, and 9D were 2.17, 2.13, 2.13, and 2.08%, respectively, against the theoretical value of 2.15%, thus validating the experimental procedure.

Rainwash Treatment

Samples of solutions 9A, 9B, 9C, and 9D were spotted on glass plates using the above-described procedure and dried at room temperature for 72 hours. The dried films were subjected to a fine spray of water using a spray bottle delivering a fine spray of water from an aspirator. The amount of water delivered was 1.49 g to 1.54 g. The remaining film was recovered into a beaker by washing the slide with a 10% EtOH aqueous solution and the washings were titrated with 0.0219 N NaOH. The endpoint of the titration was evaluated either potentiometrically or by using phenolphthalein as the indicator.

The % a.i.–1. retained was calculated by dividing the experimental concentration of a.i.1 by the theoretical or actual concentration of the a.i.1 found in the samples. Table 2 summarizes the results.

TABLE 2

Results of Rainfast Evaluation

| Composition | Spotted Samples | Contents | Weight of sample, g | Appearance of film after drying | Rainwash weight of water used, g | mL NaOH 0.0219 N | % Relative Retention |
|---|---|---|---|---|---|---|---|
| 9A | 1 | Rodeo | 0.7888 | clear dry | 1.52 | 1.05 | 30.2 |
|  | 2 | Rodeo | 0.7050 | film | 1.50 | 0.65 | 21.2 |
|  | 3 | Rodeo | 0.7068 |  | 1.50 | 0.70 | 22.5 |
|  |  | Agrimer AL25 = 0 |  |  |  |  | 24.6 ± 4.9 |
| 9B | 1 | Rodeo + | 0.7077 | clear dry | 1.50 | 1.25 | 41.3 |
|  | 2 | 0.13% | 0.7091 | film | 1.54 | 1.10 | 36.1 |
|  | 3 | Matrix | 0.7044 |  | 1.51 | 1.05 | 34.7 |
|  |  | Agrimer AL25 = 0.02 |  |  |  |  | 37.4 ± 3.5 |
| 9C of | 1 | Rodeo + | 0.700 | clear dry | 1.50 | 1.30 | 43.6 |
| Example 9 | 2 | 0.34% | 0.7004 | film | 1.52 | 1.10 | 36.6 |
|  | 3 | Matrix | 0.7062 |  | 1.49 | 1.25 | 41.3 |
|  |  | Agrimer AL25 = 0.05 |  |  |  |  | 40.5 ± 3.6 |
| 9D of | 1 | Rodeo + | 0.7033 | clear dry | 1.53 | 1.30 | 44.2 |
| Example 9 | 2 | 0.66% | 0.7091 | film | 1.50 | 1.35 | 46.1 |
|  | 3 | Matrix | 0.7070 |  | 1.50 | 1.15 | 38.9 |
|  |  | Agrimer AL25 = 0.1 |  |  |  |  | 43.1 ± 3.7 |

EXAMPLE 10

The procedure of Example 9 was repeated using the following solutions:

10A: 4.0069 g Rodeo diluted to 100 g with deionized water;
10B: 4.0018 g Rodeo and 0.1559 g of Composition I diluted to 100 g with deionized water;

10C: 4.0076 g Rodeo and 0.1133 g of the stock matrix solution of Example 1.
The results are shown in Table 3.

EXAMPLE 12

A rainfast evaluation of Rodeo with commercially available Latron B1956 as a tank mix additive was carried out.

TABLE 3

Results of Rain Wash Evaluation

| Composition | Spotted Samples | Contents | Weight of samples, g | Appearance of film | Rainwash water g | mL NaOH 0.0219 N | % Relative Retention |
|---|---|---|---|---|---|---|---|
| 10A (R1) | 1 | Rodeo | 0.7020 | clear dry film | 1.50 | 0.90 | 30.9 |
| | 2 | Rodeo | 0.7069 | | 1.51 | 0.60 | 20.3 |
| | 3 | Rodeo | 0.7020 | | 1.50 | 0.90 | 30.9 |
| | 4 | Rodeo | 0.7011 | | 1.48 | 1.00 | 34.2 |
| | | Agrimer AL25 = 0 | | | | | 29.1 ± 6.0 |
| 10B (R1) | 1 | Rodeo + | 0.7061 | clear dry film | 1.49 | 1.05 | 36.0 |
| | 2 | 0.15% | 0.7015 | | 1.48 | 1.05 | 36.0 |
| | 3 | Composition I | 0.7004 | | 1.50 | 1.10 | 35.1 |
| | 4 | | 0.7046 | | 1.51 | 1.15 | 39.5 |
| | | Agrimer AL25 = 0.024% | | | | | 36.6 ± 2.0 |
| 10C of Example 10 | 1 | Rodeo + | 0.7055 | clear dry film | 1.51 | 0.24 | 11.6 |
| | 2 | 0.11% Stock | 0.7033 | | 1.50 | 0.35 | 17.1 |
| | 3 | Matrix Solution | 0.7001 | | 1.52 | 0.35 | 17.1 |
| | 4 | | 0.7088 | | 1.49 | 0.28 | 13.6 |
| | | Agrimer AL25 = 0 | | | | | 14.9 ± 2.7 |

The difference between Examples 10B and 10C is the presence of polymer Agrimer AL25 which increases the retention of the water soluble a.i.1. from 14.9% to 36.6%. The matrix when used alone without the polymer accelerates the washing of the a.i. The polymer forms a water resistant film when used in combination with the matrix and retains the a.i.–1.

EXAMPLE 11

Evaluation of Rainfastness of Rodeo with and without Composition I

The procedure of Example 9 was repeated using compositions 9A and 9B (herein designated 11A and 11B, respectively). However, the glass plate was covered by parafilm sheets to provide a hydrophobic surface similar to that of a plant leaf surface. Composition 11A was prepared by diluting 4.000 g of Rodeo to 100 g with deionized water to form a homogeneous solution. Composition 11B was prepared by mixing 4.0101 g of Rodeo and 0.3327 g of Composition I and diluting the mixture to 100 g with deionized water. The results are shown in Table 4.

For comparison, samples of Latron B1956 stripped of its solvent and Composition I with Rodeo were prepared. The mixture was diluted before use after storing the concentrate with the adjuvant for 72 hours. The following compositions were prepared:

12A-R3: 4.00 g Rodeo diluted to 102 g with deionized water to produce a clear homogeneous solution.

12A-R4: 4.00 g Rodeo diluted to 100 g with deionized water.

12A: 4.00 g Rodeo was mixed with 0.2 g Latron B1956 diluted to 100 g to produce an emulsion.

12B: 100 g of commercial Latron was stripped of the volatile solvents by evaporation at 82° C. under 65 mm Hg vacuum for a period of 2 hours. The weight loss was 19 g. The resulting product (81 g) is designated solvent stripped Latron B1956. 1.57 g of the solvent stripped Latron was mixed with 29.26 g Rodeo and stored as a concentrate containing 95% Rodeo and 5% a solvent stripped Latron B1956.

The concentrate described above was stored for 72 hours. 4.00 g was diluted to 100 g with deionized water to produce an emulsion.

TABLE 4

Rainfast Evaluation of Rodeo with Composition I on Parafilm Surface

| Composition | Spotted Samples | Contents | Weight of sample, g | Appearance of film | Rainwash g | mL NaOH 0.0219 N | % Relative Retention |
|---|---|---|---|---|---|---|---|
| 11A | 1 | Rodeo | 0.7032 | one single | 5.05 | 0.75 | 25.2 |
| | 2 | Rodeo | 0.7079 | clear sticky | 5.00 | 0.80 | 26.4 |
| | 3 | Rodeo | 0.7066 | droplet | 5.11 | 0.42 | 20.1 |
| | | Agrimer AL25 = 0 | | | | | 23.9 ± 3.3 |
| 11B | 1 | Rodeo + | | 10–12 small | 5.09 | 1.00 | 34.12 |
| | 2 | 0.33% | | sticky | 5.12 | 1.40 | 47.4 |
| | 3 | Composition I | | droplets | 5.09 | 1.05 | 35.6 |
| | 4 | | | | 5.02 | 1.25 | 42.7 |
| | | Agrimer AL25 = 0.05% | | | | | 39.6 ± 6.0 |

12C: 22.924 g Rodeo was mixed with 2.075 g of Composition I to produce a composition containing 91.69% Rodeo and 8.30% of Composition I. The mixture was an emulsion due to the concentration of the salt (Rodeo). After 24 hours standing, it separated into two layers. However the two layers mixed completely upon two to four inversions and produced a stable emulsion that could be used within a few hours.

A 4.0 g sample of the above emulsion (obtained after storage for 72 hours and inverting 2–4 times just before withdrawing the samples) was diluted to 101.9 g with deionized water which produced a clear solution.

The compositions were evaluated for rainfastness as described in Example 9. The results are set forth in Table 5. As shown, Latron B1956 exhibited an enhanced wash-off effect for a.i.1 rather than improving its retention. The inventive composition exhibited an 80% higher retention of the a.i.–1 under the conditions of the experiments.

13B: 1 g of Prowl was mixed with 0.13 g of Composition I, Example 2, and diluted to 100 g to form an emulsion containing 0.42% pendimethalin and 0.02% Agrimer AL25 which was well dispersed in the medium.

13C: Example 13B was repeated using 0.33 g of Composition I, to produce an emulsion containing 0.42% pendimethalin and 0.05% Agrimer AL25.

13D: Example 13B was repeated using 0.66 g of Composition I, producing an emulsion containing 0.42% a.i.–2 and 0.1% Agrimer AL25.

Details of the Procedure

Emulsions were prepared as above from 13A, 13B, 13C, and 13D. While stirring, aliquots were taken. 1 g of each aliquot was diluted with EtOH to 100 g, and further diluted 10× to 50× with EtOH. UV spectra of the diluted samples were obtained. The absorbance readings at λ=238.5 nm for the samples fell in the range from 0.77 to 0.80, and the corresponding concentrations of the a.i.–2 were calculated

TABLE 5

Rainfastness Evaluation of Rodeo with Latron B1956 and Composition I (added to concentrate)

| Composition | Spotted Samples | Contents | Weight of sample, g | Appearance of film | Rain Wash water, g | mL NaOH 0.0219 N | % Relative Retention |
|---|---|---|---|---|---|---|---|
| 12A-R3 | 1 | Rodeo | 0.7544 | dry film | 1.48 | 0.95 | 30.8 |
| | 2 | Rodeo | 0.7165 | ≈1 sq. in. | 1.57 | 0.70 | 23.9 |
| | 3 | Rodeo | 0.7174 | surface area | 1.52 | 0.90 | 30.7 |
| | 4 | Rodeo | 0.7291 | (1" × 1") | 1.61 | 0.60 | 20.1 |
| | | No Agrimer AL25 | | | | | 26.4 ± 5.3 |
| 12A-R4 | 1 | Rodeo | 0.7156 | dry film | 1.51 | 0.75 | 27.1 |
| | 2 | Rodeo | 0.7080 | ≈1 sq. in. | 1.50 | 0.70 | 25.6 |
| | 3 | Rodeo | 0.7248 | surface area | 1.56 | 0.80 | 28.6 |
| | | No Agrimer AL25 | | | | | 27.1 ± 1.5 |
| 12A | 1 | Rodeo + | 0.7030 | dry film | 1.50 | 0.30 | 10.7 |
| | 2 | Latron B1956 | 0.7151 | evenly spread | 1.53 | 0.50 | 17.6 |
| | 3 | | 0.7062 | 2.5 × 2.5 sq. in. area | 1.61 | 0.35 | 12.5 |
| | | | | | | | 13.6 ± 3.6 |
| 12B | 1 | Rodeo + | 0.7138 | dry film | 1.48 | 0.35 | 12.0 |
| | 2 | Solvent Stripped | 0.7115 | evenly spread | 1.51 | 0.20 | 6.8 |
| | 3 | Latron B1956 | 0.7149 | 2" × 2" surface area | 1.50 | 0.25 | 8.5 |
| | | No Agrimer AL25 | | | | | 9.1 ± 2.7 |
| 12C | 1 | Rodeo + | 0.7036 | dry film | 1.47 | 1.25 | 46.5 |
| | 2 | Composition I added | 0.7271 | spread | 1.50 | 1.40 | 50.4 |
| | 3 | to the concentrate followed by dilution | 0.7119 | 3.5 × 3.5 sq. in. area | 1.47 | 1.40 | 51.4 |
| | | Agrimer AL25 = 0.05% | | | | | 49.4 ± 2.6 |

EXAMPLE 13

Rainfast evaluations for the inventive composition with pendimethalin (a.i.–2) were carried out. The a.i.–2 was in the commercial formulation Prowl. The procedure of Example 9 was followed. The a.i.–2 retention was determined by measuring the differential absorbance of the wash solution and EtOH at λ=238.5 nm. The following compositions were prepared for comparative evaluation.

13A: 1 g of Prowl was diluted to 100 ml with deionized water which produced a stable emulsion having an a.i.–2 concentration of 0.42%. An emulsion rather than a single phase was formed because pendimethalin is water insoluble. However, this does not affect the improvements obtained with the inventive composition.

to be 0.476%–0.492%. These values were used as the 100% retention values. The concentrations were calculated using a least squares line constructed using standard solutions of pendimethalin in EtOH. The least squares formula used was:

$$\text{absorbance} = 0.080579 \times \text{concentration (ppm)} + 0.0008785.$$

Glass plates were spotted in triplicate with about 0.3 g of the above emulsions. Films were formed by drying under ambient conditions for 72 hours. The films were rainwashed using water from an aspirated spray bottle. The remaining films were washed with 50–100 ml EtOH and the washings were collected. The absorbance of the ethanol solutions at λ=238.5 nm were measured, and the % retention was calculated. The results are summarized in Table 6. The data shows that when Agrimer AL25 is used in the form of Composition I, much higher retention of the a.i.–2 is obtained. (64% Ex. 13C as compared to 21.3% for control Ex. 13A.)

TABLE 6

Spreader-sticker Evaluation of Pendimethalin with Composition I

| Composition | Spotted Samples | Contents | weight of samples, g | appearance of film | Rain Wash water, g | vol of EtOH used, mL | absorbance at $\lambda =$ 238.5 nm | % Relative Retention |
|---|---|---|---|---|---|---|---|---|
| 13A | 1 | Pendimethalin | 0.3056 | uneven beaded | 1.08 | 50 | 0.581 | 30.8 |
|  | 2 |  | 0.3019 | film, not completely | 1.06 | 50 | 0.426 | 23.9 |
|  | 3 |  | 0.3031 | dry area 1" × 1" | 1.00 | 50 | 0.551 | 30.7 |
|  |  |  |  |  |  |  |  | 21.3 ± 3.3 |
| 13B | 1 | Pendimethalin + | 0.3018 | almost completely | 0.99 | 100 | 0.818 | 70.5 |
|  | 2 | Composition I + | 0.3010 | dry - uneven film | 1.05 | 100 | 0.943 | 81.5 |
|  | 3 | inerts Agrimer AL25 = 0.02% | 0.3030 | area 1" × 1" | 1.00 | 100 | 0.985 | 84.5 |
|  |  |  |  |  |  |  |  | 78.8 ± 7.4 |
| 13C | 1 | Pendimethalin + | 0.3067 | almost completely | 1.03 | 250 | 0.254 | 52.4 |
|  | 2 | Composition I + | 0.3075 | dry - uneven film | 1.05 | 250 | 0.339 | 69.8 |
|  | 3 | inerts Agrimer AL25 = 0.05% | 0.3025 | area 1" × 1" | 1.01 | 250 | 0.333 | 69.7 |
|  |  |  |  |  |  |  |  | 64 ± 10 |
| 13 | 1 | Pendimethalin + | 0.3010 | dry film with some | 1.00 | 50 | 0.997 | 42.0 |
|  | 2 | Composition I + | 0.3048 | sticky spots | 1.01 | 50 | 0.955 | 36.5 |
|  | 3 | inerts Agrimer AL25 = 0.1% | 0.3056 |  | 1.06 | 50 | 0.879 | 36.5 |
|  |  |  |  |  |  |  |  | 38.3 ± 3.2 |

EXAMPLE 14

An evaluation of the rainfastness of compositions of Latron B1956 and pendimethalin were carried out. Example 13 was repeated using Prowl and commercial Latron B1956. The following compositions were prepared:

14A: 1 g of Prowl was diluted to 100 g with deionized water to produce a uniform emulsion.

14B: 1 g of Prowl was mixed with 0.1 g Latron B1956 and diluted to 100 g with deionized water to produce a uniform emulsion.

14C: Example 14B was repeated using 0.2 g Latron B1956 in the place of 0.1 g Latron B1956.

In Example 13, all spots were dried outside the hood and the spray bottle was held about 1–2" away from the spot where 1 g of rain wash water was used.

In Example 14, all spots were dried inside the hood and the spray bottle was held about 4" away from the spot where 2 g of rainwater was used.

The results of the evaluation of Latron are summarized in Table 7.

TABLE 7

Spreader-sticker Evaluation of Pendimethalin with Latron B1956

| Composition | Spotted Samples | Contents | Weight of samples g | Appearance of film | Rain Wash water g | Vol of EtOH used mL | Absorbance at $\lambda =$ 238.5 nm | % Relative Retention |
|---|---|---|---|---|---|---|---|---|
| 14A | 1 | Pendimethalin | 0.3067 | Beaded no film formed | 2.26 | 100 | 0.399 | 33.9 |
|  | 2 |  | 0.3071 | 1" × 1" area | 2.31 | 100 | 0.359 | 30.3 |
|  | 3 |  | 0.3055 |  | 2.28 | 100 | 0.301 | 25.5 |
|  |  |  |  |  |  |  |  | 29.9 ± 4.2 |
| 14B | 1 | Pendimethalin + | 0.3020 | film with | 2.28 | 100 | 0.695 | 58.7 |
|  | 2 | Latron B1956 | 0.3003 | some beads | 2.31 | 100 | 0.719 | 61.0 |
|  | 3 | 0.1% | 0.3079 | area 1" × 1" | 2.27 | 100 | 0.686 | 56.9 |
|  |  |  |  |  |  |  |  | 58.9 ± 2.1 |
| 14C | 1 | Pendimethalin + | 0.3052 | uneven dry film, | 2.35 | 100 | 0.805 | 67.7 |

TABLE 7-continued

Spreader-sticker Evaluation of Pendimethalin with Latron B1956

| Composition | Spotted Samples | Contents | Weight of samples g | Appearance of film | Rain Wash water g | Vol of EtOH used mL | Absorbance at λ = 238.5 nm | % Relative Retention |
|---|---|---|---|---|---|---|---|---|
| | 2 | Latron B1956 | 0.3016 | very little beading; almost completely dry. | 2.31 | 100 | 0.808 | 69.0 |
| | 3 | 0.2% | 0.3022 | area 1" × 1" | 2.33 | 100 | 0.817 | 69.6 68.8 ± 0.97 |

EXAMPLE 15

Preparation of Modified Matrix The following weighed ingredients were introduced into a 4 oz. stoppered glass bottle:

| | |
|---|---|
| N-methylpyrrolidone | 20.0 g |
| N-octylpyrrolidone | 20.01 g |
| N-dodecylpyrrolidone | 13.01 g |
| Aqueous solution (29%) | 45.9 g |
| Sodium dodecylsulfate | |
| TOTAL | 98.92 g |

The following composition was similarly prepared except that N-methylpyrrolidone was not included.

The following compositions were obtained:

| Compositions: | 15A | 15B |
|---|---|---|
| N-methylpyrrolidone | 20.22% | 0 |
| N-octylpyrrolidone | 20.22% | 40.30 |
| N-dodecylpyrrolidone | 13.15% | 13.40 |
| Sodium dodecylsulfate | 13.45% | 13.40 |
| Water | 32.96% | 32.90 |
| TOTAL | 100.0% | 100.0 |

Composition 15A was a single-phase clear solution, while composition 15B separated into two layers on standing. Composition 15A was diluted 1/10, 1/50, 1/100 with deionized water. All of these diluted three samples were clear when observed up to 24 hours.

Composition 15A was used as an alternate matrix to solubilize Agrimer AL25.

EXAMPLE 16

To 47.51 g of composition 15A, 2.5 g of solid Agrimer AL25 were added and stirred in an orbital shaker for 4 hours at 350 RPM. 50.03 g of a clear homogeneous solution were obtained. This solution was diluted with deionized water in ratios of 1/10, 1/500, and 1/1000. No separation was observed in the diluted solution after for 24 hours.

EXAMPLE 17

Example 16 was repeated but using 45 g of composition 15A and 5.00 g of Agrimer AL25. The resulting composition remained a homogeneous single phase solution. On dilution with deionized water at ratios of 1/10, 1/500, and 1/1000, no separation was observed.

EXAMPLE 18

Example 16 was repeated using 42.5 g of composition 15A and 7.51 g of Agrimer AL25. The resulting polymer solution was clear and homogeneous and did not show any separation on dilution with deionized water at ratios of 1/10, 1/500, and 1/1000.

EXAMPLE 19

A series of examples were carried out using various alkyl pyrrolidones, including N-methyl pyrrolidone, N-octyl pyrrolidone, and N-dodecyl pyrrolidone. The N-dodecyl pyrrolidone exhibits stronger surfactant properties whereas the N-octyl exhibits stronger wetting properties, i.e., it wets hydrophobic surfaces as evidenced by the Draves Wetting test. The N-methyl pyrrolidone, on the other hand, is a better solvent and also provides enhanced plant and leaf penetration properties. I have found that a particularly desirable composition contains about 0.1 to 10, and preferably, about 0.5 to 2 parts of N-dodecyl pyrrolidone, and 0.1 to 10, and preferably, about 0.5 to 2 parts of N-methylpyrrolidone to 1 parts of N-octyl pyrrolidone, respectively. This composition provides not only enhanced leaf penetration, but also, better spreading due to the N-dodecyl component. Additionally, this composition allows increased amounts of the polymer component to be included in a single phase system.

For this purpose, Example 16 was repeated using 40.03 g of composition 15A and 10.01 g of Agrimer AL25. A homogeneous polymer solution was obtained after stirring for 4 hours in an automatic orbital shaker. No separation on dilution with deionized water at ratios of 1/10, 1/500, and 1/1000 was observed.

Compositions of Examples 16, 17, 18, and 19 and results of dilution are shown in Table 8.

TABLE 8

Additional Compositions of Single Phase Systems Containing Agrimer AL25 in an Aqueous Medium

| Composition Ingredients | Weight % | | | |
|---|---|---|---|---|
| | Example 16 | Example 17 | Example 18 | Example 19 |
| N-methylpyrrolidone | 19.2 | 18.2 | 17.19 | 16.18 |
| N-octylpyrrolidone | 19.2 | 18.2 | 17.19 | 16.18 |
| N-dodecylpyrrolidone | 12.49 | 11.84 | 11.18 | 10.52 |

TABLE 8-continued

Additional Compositions of Single Phase Systems Containing Agrimer AL25 in an Aqueous Medium

| Composition Ingredients | Weight % | | | |
|---|---|---|---|---|
| | Example 16 | Example 17 | Example 18 | Example 19 |
| SDS | 12.78 | 12.10 | 11.43 | 10.76 |
| Agrimer AL25 | 5.0 | 10.0 | 15.0 | 20.0 |
| Water | 31.31 | 29.66 | 28.02 | 26.37 |
| TOTAL | 100.00 | 100.00 | 100.00 | 100.00 |
| Physical State Dilution | | | | |
| 1/10 | clear | clear | clear | clear |
| 1/500 | clear | clear | clear | clear |
| 1/1000 | clear | clear | clear | clear |

EXAMPLE 20

A series of microemulsions were prepared using the compositions of Examples 9B, 9D, 11B, 12C and 13B, with the exception that in place of Composition I, the composition of Example 19 was utilized. The compositions thus obtained were tested for rainfastness and produced results essentially similar to those depicted for the compositions 9B, 9D, 11B, 12C and 13B.

EXAMPLE 21

Compositions I of Example 19 were prepared as follows:

The commercially available 50% solution of Agrimer AL25 in isopropylalcohol was mixed with the appropriate quantity of N-octyl pyrrolidone or N-dodecyl pyrrolidone. The mixture was then subjected to distillation conditions to distill off the isopropylalcohol either at atmospheric or under reduced pressure (17 mm Hg). When all of the isopropylalcohol was removed, the remaining ingredients constituting the compositions as shown were added. These compositions were evaluated for rainfastness in the manner described above by repeating Examples 9A, 9D, 13A and 13B. The results obtained were essentially similar to those of these examples. Accordingly, it is possible to add the polymer in an in silt manner as well as the dried polymer as described in connection with the preparation of the matrix.

EXAMPLE 22

A freeze dried formulation in accordance with the invention was prepared as follows:

Phosphonomethylglycine, 169 g (1 mole), was blended with $NaHCO_3$, 168 g (2 moles), both of these being solids, to produce a mixture which forms the sodium salt of the phosphonomethylglycine on contact with water. The mixture was ground to a fine powder.

80 g of this mixture was then blended with 20 g of the inventive composition (Composition I), followed by the addition of 50 g of water. This composition was subjected to freeze-drying and produced 70 g of a free-flowing powder product.

Upon mixing with water on the basis of 1% by weight of the free-flowing powder product, a clear liquid (single phase) was obtained. This procedure thus allows for preparation of an inventive composition which is in dry form and thus easily transportable and which can, at the use or field site, be converted to a clear liquid upon the addition of water. It is particularly convenient as the dry inventive composition can be packaged in predetermined weights in a water-soluble container, e.g., a bag, which can simply be added to a dilution tank in the field.

If the active ingredient is water-soluble, then the use of bicarbonate or other soluble salt-forming reactant is not necessary. If effervescence is desired to enhance the rate of dissolution of the solid on the addition of water, an effervescing component, e.g., citric acid, or additional of bicarbonate may be added.

EXAMPLE 23

A series of tests were carried out to evaluate the effect of the inventive compositions on the efficacy of two commercially available herbicides, namely, Roundup and Gramoxone for Bahia grass and broad-leaf weed control.

The tests were conducted in Lake Alfred, Fla. in citrus groves having trees of two years of age. The chemicals applied, conditions and application parameters at the time of application were as follows:

The concentrates were diluted so as to provide 1 lb Glyphosate at 20 gallons per acre and 0.625 lbs. Paraquat at 20 gallons per acre.

| | |
|---|---|
| Weather | clear |
| Humidity | 50% |
| Wind velocity | calm |
| Water source | well |
| pH | 7.1 |
| Volume of spray | 20 GPA (Gallons per acre) |
| Spray pressure | 35 psi |
| Source of pressure | compressed air |
| Nozzle type/size | Teejet tips 8001 |
| Nozzle spacing | 10 inches |
| Type of sprayer | Tractor mounted boom sprayer |
| Tractor speed | 2.73 mph |
| Plot size | 45 × 10 ft. |
| Number of treatments | 31 |
| Number of replications | 3 |
| Total number of plots | 93 |
| Stage of weed growth | 4–6" high |
| Major weeds | Broadleaf weeks: camphor weeks Florida pusley Jerusalem oak lambsquarters pigweed Spanish needles tea weed |

The application was carried out in one day from 8:00 A.M. to 5:00 P.M.

Tables 9 and 10 show the effects of the treatment 5 with controls and the inventive compositions on the growth of the respective weeds over a period of 63 days.

The herbicide was mixed with either inventive Composition I or Complex so as to give the active ingredient concentrations (a.i.1) as indicated on Table 8. Complex had the following composition:

| | |
|---|---|
| Alkyl polyoxyethylene esters Polymerized resins and fatty acid | 16.6% |
| Reactive amines | 5.2% |
| Aromatic petroleum solvent | 4.9% |
| Inert solvents | 72.3% |

TABLE 9

Evaluation for Bahia grass control (%) Kill

| | Percent Kill Days after Treatment | | | | | |
|---|---|---|---|---|---|---|
| Treatments: | 3 | 7 | 21 | 42 | 63 | Notes |
| 1. Composition I 0.25% | 0 | 0 | 0 | 0 | 0 | A |
| 2. Complex 0.25% | 0 | 0 | 0 | 0 | 0 | B |
| 3. Glyphosate 1.0 lb ai/A | 5 | 25 | 50 | 40 | 25 | C |
| 4. Glyphosate 1.0 lb ai/A + Composition I 0.0625% | 5 | 25 | 80 | 50 | 40 | D |
| 5. Glyphosate 1.0 lb ai/A + Composition I 0.125% | 5 | 25 | 85 | 60 | 50 | E |
| 6. Glyphosate 1.0 lb ai/A + Composition I 0.25% | 5 | 40 | 100 | 80 | 90 | F |
| 7. Glyphosate 1.0 lb ai/A + Complex 0.0625% | 5 | 25 | 60 | 40 | 25 | G |
| 8. Glyphosate 1.0 lb ai/A + Complex 0.125% | 5 | 25 | 70 | 40 | 25 | H |
| 9. Glyphosate 1.0 lb ai/A + Complex 0.25% | 5 | 30 | 90 | 60 | 80 | I |
| 10. Paraquat 0.625 lb ai/A | 50 | 50 | 40 | 30 | 10 | J |
| 11. Paraquat 0.625 lb ai/A + Composition I 0.0625% | 70 | 70 | 60 | 35 | 10 | K |
| 12. Paraquat 0.625 lb ai/A + Composition I 0.125% | 80 | 80 | 70 | 55 | 20 | L |
| 13. Paraquat 0.625 lb ai/A + Composition I 0.25% | 100 | 100 | 95 | 75 | 50 | M |
| 14. Paraquat 0.625 lb ai/A + Complex 0.0625% | 80 | 80 | 60 | 30 | 10 | N |
| 15. Paraquat 0.625 lb ai/A + Complex 0.125% | 80 | 80 | 60 | 30 | 10 | O |
| 16. Paraquat 0.625 lb ai/A + Complex 0.25% | 90 | 90 | 80 | 60 | 40 | P |
| 17. Untreated control | 0 | 0 | 0 | 0 | 0 | |

TABLE 10

Evaluation for Broadleaf Weed Control (%) Kill

| | Percent Kill Days after Treatment | | | | | |
|---|---|---|---|---|---|---|
| Treatments: | 3 | 7 | 21 | 42 | 63 | Notes |
| 1. Composition I 0.25% | 0 | 0 | 0 | 0 | 0 | A |
| 2. Complex 0.25% | 0 | 0 | 0 | 0 | 0 | B |
| 3. Glyphosate 1.0 lb ai/A | 5 | 10 | 50 | 20 | 10 | C |
| 4. Glyphosate 1.0 lb ai/A + Composition I 0.0625% | 5 | 15 | 70 | 30 | 15 | D |
| 5. Glyphosate 1.0 lb ai/A + Composition I 0.125% | 5 | 20 | 75 | 35 | 15 | E |
| 6. Glyphosate 1.0 lb ai/A + Composition I 0.25% | 10 | 50 | 100 | 60 | 25 | F |
| 7. Glyphosate 1.0 lb ai/A + Complex 0.0625% | 5 | 15 | 60 | 25 | 10 | G |
| 8. Glyphosate 1.0 lb ai/A + Complex 0.125% | 5 | 15 | 65 | 30 | 10 | H |
| 9. Glyphosate 1.0 lb ai/A + Complex 0.25% | 5 | 45 | 90 | 50 | 20 | I |
| 10. Paraquat 0.625 lb ai/A | 50 | 50 | 30 | 10 | 5 | J |
| 11. Paraquat 0.625 lb ai/A + Composition I 0.0625% | 60 | 60 | 45 | 20 | 5 | K |
| 12. Paraquat 0.625 lb ai/A + Composition I 0.125% | 70 | 70 | 50 | 25 | 5 | L |
| 13. Paraquat 0.625 lb ai/A + Composition I 0.25% | 100 | 100 | 80 | 50 | 10 | M |
| 14. Paraquat 0.625 lb ai/A + Complex 0.0625% | 50 | 50 | 40 | 15 | 5 | N |
| 15. Paraquat 0.625 lb ai/A + Complex 0.125% | 55 | 55 | 45 | 25 | 5 | O |
| 16. Paraquat 0.625 lb ai/A + Complex 0.25% | 90 | 90 | 60 | 40 | 5 | P |
| 17. Untreated control | 0 | 0 | 0 | 0 | 0 | Q |

NOTES FOR TABLES 9 AND 10

A   Composition I was diluted at the rate of 0.025 gallon in 10 gallons of water to produce 0.25% solution.
B   "Complex" was diluted as in Example 23A.
C   Commercial Roundup containing 4 lbs. a.i. per gallon was diluted to 80 gal. to be sprayed in 4 acres.
D   Composition C was prepared except 0.05 gal. of Composition I was added to 1 gal. of Roundup and diluted to 80 gal. to be sprayed in 4 acres.

TABLE 10-continued

| | |
|---|---|
| E | Composition D was altered by using 0.1 gal. of Composition I instead of 0.05 gal. |
| F | Composition D was altered by using 0.2 gal. of Composition I instead of 0.05 gal. |
| G | Composition D was altered by using 0.05 gal. Complex in the place of Composition I. |
| H | In 20 gal., 0.1 gal. Complex was used in the place of 0.05 gal. |
| I | In 20 gal., 0.2 gal. Complex was used in the place of 0.05 gal. |
| J | Commercial Gramoxone containing 2 bls. a.i. per gal was diluted at the following rate: 1.25 gal. was diluted to 80 gal. to be sprayed in 4 acres. |
| K | J was modified by adding 0.05 gal. of Composition I before final dilution. |
| L | K was modified by using 0.1 gal. of Composition I in the place of 0.05 gal. |
| M | K was modified by using 0.2 gal. of Composition I in the place of 0.05 gal. |
| N | K was modified by using 0.05 gal. of Complex in the place of Composition I. |
| O | N was modified by using 0.1 gal. of Complex in the plaae of 0.05 gal. |
| P | N was modified by using 0.2 gal. of Complex in the place of 0.05 gal. |

These results show that an enhanced biological efficacy is obtained when the a.i. is used as an adjuvant in the inventive composition. In particular the effect of the a.i. is accelerated and/or increased. Thus, with the present invention, it becomes possible to decrease the amount of active ingredient and still achieve a high efficacy.

What is claimed is:

1. A composition comprising:

a. a long chain alkylpyrrolidone having the formula:

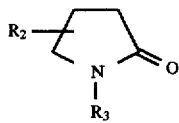

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14;

b. an anionic surfactant other than the long-chain alkylpyrrolidone;

c. a film-forming water insoluble graft polymer from 20 to 80% of N-vinylpyrrolidone and from 80 to 20% of an α-olefin, the latter monomer containing up to 20 carbon atoms; and d. an agriculturally active chemical;

the relative amounts of the components being such that the composition forms a rainfast microemulsion or emulsion when added to water.

2. A solid composition comprising a. a long chain alkylpyrrolidone having the formula:

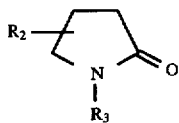

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14;

b. an anionic surfactant other than the long-chain alkylpyrrolidone;

c. a film-forming water insoluble graft polymer from 20 to 80% of N-vinylpyrrolidone and from 80 to 20% of an α-olefin, the latter monomer containing up to 20 carbon atoms; and d. sodium bicarbonate;

which composition, on the addition of water thereto, produces a clear liquid.

3. A solid composition comprising a. a long chain alkylpyrrolidone having the formula:

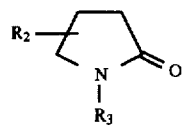

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14;

b. an anionic surfactant other than the long-chain alkylpyrrolidone;

c. a film-forming water insoluble graft polymer from 20 to 80% of N-vinylpyrrolidone and from 80 to 20% of an α-olefin, the latter monomer containing up to 20 carbon atoms;

d. an agriculturally active chemical; and e. sodium bicarbonate;

the relative amounts of the components being such that the composition forms a clear liquid on the addition of water having rainfast properties when applied to a substrate.

4. A composition comprising a. N-dodecylpyrrolidone and N-octylpyrrolidone;

b. an anionic surfactant other than the long-chain alkylpyrrolidone;

c. a film-forming water-insoluble graft polymer from 20 to 80% of N-vinylpyrrolidone and from 80 to 20% of an α-olefin, the latter monomer containing up to 20 carbon atoms; and d. N-methylpyrrolidone;

wherein the relative amounts of the components are such that the composition on dilution with water forms a clear liquid and wherein the N-dodecylpyrrolidone and N-methylpyrrolidone are each present in a weight ratio of from about 0.1 to 10 part to 1 part N-octylpyrrolidone.

5. The composition of claim 1 wherein the water-insoluble polymer is a graft copolymer of N-vinyl-pyrrolidone and an alpha olefin containing 16 carbon atoms in a weight ratio of 50:50 and having a number average molecular weight of about 9500.

6. The composition of claim 4 wherein the ratio is from about 0.5 to 2 parts each of N-dodecyl pyrrolidone and N-methyl pyrrolidone to 1 part of N-octyl pyrrolidone.

7. The composition of claim 1 which further comprises water.

8. The composition of claim 1 which comprises from about 2 to 90 percent alkylpyrrolidone, from about 2 to 30 percent surfactant, from about 1 to 50 percent water-insoluble polymer and from about 1 to 50 percent water, all percents being by weight based on the total weight of the composition.

9. The composition of claim 1 wherein the water insoluble polymer is a graft copolymer of N-vinyl pyrrolidone and a alpha olefin having up to 20 carbon atoms and the polymer having a number average molecular weight up to about 50,000.

10. The composition of claim 9 wherein the alpha olefin contains from 6 to 20 carbon atoms.

11. The composition of claim 9 wherein the N-vinyl pyrrolidone is present in an amount of more than 20 percent on a weight basis in the graft copolymer.

12. The composition of claim 9 wherein the N-vinyl pyrrolidone is present in an amount of more than 50 percent on a weight basis in the graft copolymer.

13. The composition of claim 9 wherein $R_2$ is hydrogen and $R_3$ is and alkyl containing from 8 to 12 carbon atoms.

14. The composition of claim 9 wherein the water-insoluble polymer is a graft copolymer of N-water-insoluble vinylpyrrolidone and an alpha olefin containing 16 carbon atoms in a weight ratio of 50:50 and having a number average molecular weight of about 9500.

15. The composition of claim 14 wherein the agriculturally active chemical is selected from the group consisting of pesticides and herbicides.

16. The composition of claim 15 wherein the long-chain alkyl pyrrolidone is selected from the group consisting of N-ocrylpyrrolidone, N-dodecylpyrrolidone, and mixtures thereof.

17. The composition of claim 15 which further comprises N-methyl pyrrolidone in an amount effective to solubilize the long-chain alkyl pyrrolidone.

18. The composition of claim 15 wherein the weight ratio is from about 0.5 to 2 parts each of N-dodecyl pyrrolidone and N-methyl pyrrolidone to 1 part of N-octyl pyrrolidone.

19. The composition of claim 15 wherein the agriculturally active chemical is selected from the group consisting of the isopropylamine salt of phosphonomethylglycine, pendimethalin, and 1,1-dimethyl-4,4'-bipyridinium dichloride.

20. The composition of claim 1 wherein the water-insoluble polymer forms a film having adhesive properties.

21. The composition of claim 1 wherein the water-insoluble polymer forms a film having protective properties.

22. The composition of claim 1 wherein the water-insoluble polymer forms a film having decorative properties.

23. The composition of claim 1 wherein the water-insoluble polymer forms a film having lubricating properties.

24. The composition of claim 1 wherein the water-insoluble polymer forms a film having hydrophobic properties.

25. The composition of claim 1 wherein the water-insoluble polymer forms a film having hydrophilic properties.

26. A method for forming a polymeric film on a substrate comprising applying the composition of claim 1 onto the substrate and removing the water.

27. A method for treating plants or soil with an agriculturally active chemical comprising applying the composition of claim 1 to the plant or soil.

28. A method for forming the solid composition of claim 3 comprising the steps of A) mixing a solid agriculturally active chemical in particulate form with $NaHCO_3$ in particulate form;

B) mixing the product from step A) with a composition comprising a. a long chain alkylpyrrolidone having the formula:

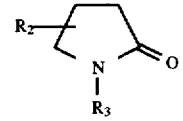

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sun of the carbon atoms in $R_2$ and $R_3$ cannot exceed 14;

b. a surfactant; and c. a film-forming water insoluble polymer; and d. water; and C) freeze-drying the product from step B).

29. The composition of claim 1 wherein the long chain alkyl-pyrrolidone is N-octylpyrrolidone.

30. The composition of claim 15 wherein the long chain alkylpyrrolidone is N-octylpyrrolidone.

31. The composition of claim 30 which contains N-dodecylpyrrolidone and N-methyl pyrrolidone, each in a weight ratio of from about 0.1 to 10 parts to 1 part N-octyl pyrrolidone.

* * * * *